United States Patent [19]
Dohi et al.

[11] Patent Number: 6,008,206
[45] Date of Patent: Dec. 28, 1999

[54] SODIUM ALENDRONATE PREPARATION FOR LOCAL ADMINISTRATION

[75] Inventors: Masahiko Dohi; Yuji Makino; Takao Hujii, all of Tokyo, Japan

[73] Assignee: Merck & Co., Inc., Rahway, N.J.

[21] Appl. No.: 09/086,173

[22] Filed: May 28, 1998

Related U.S. Application Data

[63] Continuation of application No. 08/821,754, Mar. 20, 1997, abandoned.

[51] Int. Cl.$^6$ .................................................... A61K 31/66
[52] U.S. Cl. ................................................................ 514/108
[58] Field of Search ............................................... 514/108

[56] References Cited

U.S. PATENT DOCUMENTS

| | | | |
|---|---|---|---|
| 4,621,077 | 11/1986 | Rosini et al. | 514/108 |
| 5,270,365 | 12/1993 | Gertz et al. | 514/108 |
| 5,668,120 | 9/1997 | Shinoda et al. | 514/102 |

*Primary Examiner*—Phyllis G. Spivack
*Attorney, Agent, or Firm*—Anthony D. Sabatelli; Melvin Winokur

[57] ABSTRACT

The object of the present invention is to provide a preparation for local administration to permit selective delivery of an effective amount of sodium alendronate to the bone site where bone resorption is accentuated.

2 Claims, No Drawings

SODIUM ALENDRONATE PREPARATION FOR LOCAL ADMINISTRATION

CROSS REFERENCE TO RELATED APPLICATIONS

This is a continuation of application Ser. No. 08/821,754, filed Mar. 20, 1997, abandoned.

CONSTITUTION

A preparation for local administration which comprises an effective amount of sodium alendronate and a medium such as water, propylene glycol or a pharmaceutically acceptable buffer. The preparation is suitable for administering percutaneously by iontophoresis.

DETAILED DESCRIPTION OF THE INVENTION

1. Industrial Field of Application

The present invention relates to drug therapy by sodium alendronate. Further the present invention relates to a sodium alendronate preparation to provide selective and safe delivery of an effective amount of sodium alendronate to the bone site in a body which needs sodium alendronate and in which bone resorption is accentuated by local and percutaneous administration.

2. Background of the Invention

Sodium alendronate is a biphosphonate compound represented by the following formula (formula 1):

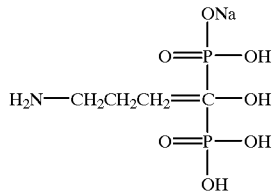

Sodium alendronate inhibits bone resorption by osteoclast, in vivo, and can be used as therapeutic agent for hypercalcemia, Paget's disease and osteoporosis (History of Medical Science, 165(9), pp. 674–678, 1993). In recent years, there have been note worthy cases where local accentuation of bone resorption is observed in such diseases as osteoarthritis (OA) and chronic articular rheumatism. Sodium alendronate is expected to provide an effective therapeutic agent for these diseases.

PROBLEMS TO BE SOLVED BY THE INVENTION

Preparations for sodium alendronate are being developed as therapeutic agents for parenteral and oral administration. In the case of such diseases as osteoporosis, it is difficult to predict the affected site in the bone structure of the body. Such diseases requires systemic administration by parenteral or oral administration. However, systemic administration of sodium alendronate is not required in cases where local accentuation of bone resorption is observed in diseases such as osteoarthritis (OA) and chronic articular rheumatism, and cases where accentuation of bone resorption is locally observed in the cartilaginous tissue in contact with the artificial joint having been installed. Local delivery to the site where bone resorption is accentuated provides an effective administration which reduces the adverse affects.

Furthermore, inhibition of bone resorption by sodium alendronate is caused by the characteristics on the crystal surface being changed by sodium alendronate adsorbed into bone hydroxyapatite, and by direct action to osteoclast. Namely, sodium alendronate need not be present throughout the blood; it is important that it is distributed on the bone surface.

In the Japanese patent Laid-Open No. 44328/1991, Pil George Ferini et al. show that the biphosphonates containing sodium alendronate can be absorbed percutaneously. However, said patent is intended for systemic action by local administration; it is different from the selective delivery to the site where bone resorption is accentuated, as in the present invention. Furthermore, mere percutaneous administration only allows sodium adendronate to pass through the skin. It is immediately absorbed into the blood vessel and is distributed throughout the body. Thus, this method is not different from the conventional parenteral and oral administration.

G. B. Kasting et al. reports that the same blood profile as that of parenteral administration by percutaneous delivery method using iontophoresis is shown by the etidronate which is one of the biphosphonates, the same as sodium alendronate (J. Membrane Science 35, 161–165, 1988). However, even if their report shows that the biphosphonate is delivered percutaneously to the blood, they are not interested in local distribution at all. Regarding distribution to the entire bone, they have not found any difference between the percutaneous administration by iontophoresis and intravenous injection.

In other words, G. B. Kasting et al. have found that a biphosphonate pertaining to the same type as sodium alendronate can be percutaneously administered to the whole body by iontophoresis in the same way as parenteral and oral administration. Unfortunately, however, they have failed to note that the compound is distributed in the vicinity of the site where it was administered. This is because of the following reason: According to the conventional technology, it was quite natural to consider that these compounds passed through the epidermis and dennis by iontophoresis, and were absorbed into the blood layer. It would have been difficult to assume direct distribution to the bone through subcutaneous tissue.

MEANS OF SOLVING THE PROBLEMS

The present inventors have made a strenuous effort to study the preparation of sodium alendronate for selective administration of a therapeutically effective amount of sodium alendronate to the bone where bone resorption is accentuated and cartilaginous tissue. The present inventors have found out a sodium alendronate preparation which can be effectively administered to the affected site, where said preparation passes through the epidermis, dermis, blood layer and hypodermic tissue through percutaneous delivery by iontophoresis into the body from the biological integument in the vicinity of the bone site where bone resorption is accentuated.

The present invention, therefore, provides a pharmaceutical preparation of sodium alendronate which can reduces the dose of sodium alendronate by systemic administration such as parenteral and oral administration, and can be expected to minimize adverse effect.

The present invention is intended to provide drug therapy by sodium alendronate, and is a pharmaceutical preparation for a local administration comprising sodium alendronate and a medium to provide selective delivery of an effective amount of sodium alendronate for medical treatment to the bone site where bone resorption is accentuated.

More particularly, the present invention is intended to provide drug therapy by sodium alendronate, and is pharmaceutical preparation for a local administration comprising sodium alendronate and a medium to provide selective delivery of an effective amount of sodium alendronate for medical treatment, preferably by iontophoresis (electric delivery method), to the bone site where bone resorption is accentuated.

In the present invention, the bone site where bone resorption is accentuated includes the following examples where such symptoms are involved; (1) the bone site with resorption accentuated by osteolysis locally occurring at the cartilaginous tissue in contact with the artificial joint which has been installed to the joint site such as femoral bone, (2) the bone site with resorption accentuated by osteoclasis accompanying local cartilaginoclasis such as osteoarthritis (OA) or chronic articular rheumatism (RA), and (3) the bone site with resorption accentuated by bone destruction of the dentin resulting from alveolar pyorrhea.

The term "medium" used in the present invention refers to conductive material including water, methanol, ethanol, propylene glycol, a pharmaceutically acceptable buffer and a mixture thereof; it particularly refers to such medium without biological toxicity. Of these materials, the pharmaceutically acceptable buffer includes phosphoric acid buffer or acetic acid buffer. The pH value of these buffer solutions should be from 3 to 12, preferably from 4 to 10, more preferably from 6 to 8.

These medium can be in sol or gel form resulting from addition of the following compounds; (1) natural high molecular compounds such as starch and sodium alginate, (2) semi-synthetic polymers such as crystalline-cellulose, dextrin, gelatin, starch derivative and cellulose derivative, or (3) polymers such as polyvinyl pyrrolidone, polyethylene glycol and polyvinyl alcohol.

Furthermore, the following can also be used as the medium; (1) a medium chain fatty acid ester such as liquid paraffin and migriol, (2) an oily solvent such as silicone oil and natural wax; (3) a pharmaceutically acceptable location base obtained by adding solvent, emulsifier and suspending agent to water based solution and making them uniform; (4) a pharmaceutically acceptable ointment base including hydrophilic ointment, hydrophilic vaseline and hydrous lanolin; and (5) a pharmaceuticany acceptable cream base including vanishing cream and cold cream.

In addition to said media, sodium alendronate preparation according to the present invention may contain (1) a fatty acid ester such as isopropyl myristate, (2) a high-grade alcohol, (3) a medium chain fatty acid glyceride such as monoglyceride caprylate, (4) a terpene and (5) an absorbefacient such as dimethyl sulphoxide.

Iontophoresis, for example, provides an effective way for selective delivery of sodium alendronate within the body to the bone site with accentuated resorption locally by percutaneous means. Iontophoresis is referred to as ion osmosis as well as electric delivery, and can be defined as introduction of ionic or water soluble drugs into the body through biological integument for therapeutical purposes. Diversified types of iontophoresis are available since the devices related to iontophoresis have been much improve and upgraded since the early 1900s (See "Drug Delivery Devices" edited by Praveen Yyle, 1988, Marceldekker Inc. pp. 421–455). However, it is basically composed of power source, a pair of electrodes connected thereto, and conductive medium installed between said electrodes and biological integument.

Electrodes to be used are made of platinum, carbon or silver/silver chloride; any material will do so long as it is electrically conductive. Furthermore, conductive medium installed between said electrodes and biological integume includes natural resin polysaccharide such as sterculia gam (karaya gum), tragacanth gum and xanthan gum; a vinyl based resin such as partially saponated substance of polyvinyl alcohol, polyvinyl formal and polyvinyl methyl ether; acryl based resin including polyacryl acid, its sodium salt, polyacrylamide and its partial hydrolysate; various types of natural or synthetic hydrophilic resins; which are plasticized to gel state by water and alcohol such as ethylene glycol and glyceline. It further includes the sponge or porous material such as conductive gel, paper mesh such as blotting paper, cloth mesh such as gaze, fibrous mesh such as absorbent cotton, continuous foam of synthetic resin or water absorbent resin which is impregnated with electrically conductive aqueous medium such as water, methanol, ethanol, propylene glycol, a pharmaceutically acceptable buffer solution or a mixture thereof.

Iontophoresis can be achieved by application of electric current by forming an power circuit according to the following method; thereby allowing delivery of sodium alendronate into the body: <1> Aqueous solution containing sodium alendronate or the batch containing water soluble gel provided with electrode are attached to two positions of the biological integument; or <2> aqueous solution containing sodium alendronate or the batch containing water soluble gel provided with electrode, and the batch without containing drug provided with electrode are attached to one each position of the biological integument.

Application of electric current can be provided by the following method: In the case of <1>, a circuit is formed by DC power to switch the polarity at an interval of 5 through 20 minutes. In the case of <2>, a circuit by DC power is formed, and electric current is applied under that condition; or a circuit by DC power is formed to switch the polarity at an interval of 5 through 20 minutes, or a circuit by pulse power is formed. Preferably for <1>, a circuit is formed by DC power to switch the polarity at an interval of 5 through 20 minutes.

Preferably the current of 0.01 mA through 50 mA, or more preferably 0.5 mA through 20 mA, should be applied.

In the preparation, the preferred amount of therapeutically effective amount of sodium alendronate is 0.5 mg through 100 mg, and more preferred amount is 0.5 mg through 50 mg.

EXAMPLES

The following describes the present invention with reference to the following examples, without being restricted to such examples:

Example 1

Formulating a Preparation Using Water Based Medium and a Test Example (a) Formulating a preparation 9.9 mg of sodium alendronate and 0.1 mg of sodium alendronate labeled by $^{14}C$ were measured out accurately and resolved into purified water, thereby formulating 10 mg/ml of water based preparation containing sodium alendronate.

(b) Test example

A Wistar male rat (three-week old rat weighing 110 through 130 g) was fixed on the backward posture, and a drug reservoir cell (volume: 1.1 cm diam. 0.5 cm=0.47 cm3) with platinum electrode was installed inside the right thigh using the AloneApha (trade name manufactured by Sankyo Co., Ltd.) for use in medical operation. A control electrode (10% polyvinyl alcohol gel) with platinum electrode was installed outside the right thigh. Each electrode was connected to the anode and cathode of the DC power supply to form an power circuit. The drug reservoir cell was filled with 0.47 ml of water based preparation formulated in (a). Then current of 0.1 mA was applied for four hours.

Table 1 illustrates the amount of sodium alendronate absorbed into the tissue of the bone (right thigh) in the vicinity of the administered site and the bone (left thigh) located far from the administered site two through four hours after start of electric current application. The amount of sodium alendronate absorbed into the tissue was calculated by measuring the radioactivity of $^{14}$C-labeled sodium alendronate using the liquid scintillation counter.

TABLE 1

| Hour | 2.0 | 4.0 |
|---|---|---|
| Close to administered site (right thigh) (ng/mg) | 36.64 | 79.45 |
| Far from administered site (left thigh) (ng/mg) | 2.13 | 3.57 |

Example 2

Ointment agent was formulated according to the following composition table. White vaseline and liquid paraffin were heated and molten, and were half-cooled. Then water solution of sodium alendronate was added to it, and was mixed. It was kneaded until it was made uniform throughout the chamber.

| Component | Weight |
|---|---|
| Sodium alendronate | 0.01 g |
| White vaseline | 0.95 g |
| Liquid paraffin | 0.05 g |

Example 3

Lotion base was formulated according to the following composition table. White bees wax, cetyl alcohol and sodium lauryl sulfate were heated to 70 degrees Celsius and molten, and were made into oil phase. Sodium alendronate and glyceline were mixed with each other in purified water, and were heated to 75 degrees Celsius to be made into aqueous phase. Oil phase was gradually added to aqueous phase, and was mixed until emulsification was completed to obtain uniform liquid.

| Component | Weight |
|---|---|
| Sodium alendronate | 0.01 g |
| White bees wax | 0.1 g |
| Cetyl alcohol | 1.5 g |
| Sodium lauryl sulfate | 0.5 g |
| Glyceline | 5.0 ml |
| Purified water | 100 ml |

What is claimed is:

1. A non-systemic pharmaceutical preparation for local iontophoretic administration comprising sodium alendronate and a medium to provide selective non-systemic iontophoretic delivery of an effective amount of sodium alendronate for medical treatment to a bone site where bone resorption is accentuated, said bone site being selected from a bone site other than the alveolar bone.

2. A method for selectively delivering sodium alendronate percutaneously through a biological integument to an underlying bone tissue site where bone resorption is accentuated, said bone site being selected from a gone site other than the alveolar bone, comprising:

(a) contacting said biological integument with a composition comprising sodium alendronate and a conductive medium to provide iontophoretic delivery of said alendronate, and (b) applying an electric current to said composition.

* * * * *

UNITED STATES PATENT AND TRADEMARK OFFICE
CERTIFICATE OF CORRECTION

PATENT NO. : 6,008,206
DATED : 12/28/1999
INVENTOR(S) : Masahiko Dohi et al.

It is certified that error appears in the above-identified patent and that said Letters Patent is hereby corrected as shown below:

At p. 1, Section [75], delete the name "Takao Hujii", and insert therefor -- Takao Fujii --.

Signed and Sealed this

First Day of August, 2000

*Attest:*

Q. TODD DICKINSON

*Attesting Officer*   *Director of Patents and Trademarks*